United States Patent
Charles et al.

(10) Patent No.: US 9,955,865 B2
(45) Date of Patent: May 1, 2018

(54) METHOD AND SYSTEM TO DETECT OPHTHALMIC TISSUE STRUCTURE AND PATHOLOGIES

(71) Applicant: NOVARTIS AG, Basel (CH)

(72) Inventors: Steven T. Charles, Memphis, TN (US); Michael James Papac, North Tustin, CA (US); Michael Yadlowsky, Sunnyvale, CA (US)

(73) Assignee: Novartis AG, Basel (CH)

( * ) Notice: Subject to any disclaimer, the term of this patent is extended or adjusted under 35 U.S.C. 154(b) by 394 days.

(21) Appl. No.: 13/860,626

(22) Filed: Apr. 11, 2013

(65) Prior Publication Data
US 2014/0307078 A1    Oct. 16, 2014

(51) Int. Cl.
*A61B 3/113*    (2006.01)
*A61B 3/10*    (2006.01)
*G06T 7/00*    (2017.01)

(52) U.S. Cl.
CPC ............ *A61B 3/102* (2013.01); *G06T 7/0012* (2013.01); *G06T 2207/10028* (2013.01); *G06T 2207/10101* (2013.01); *G06T 2207/30041* (2013.01)

(58) Field of Classification Search
CPC ..................................................... A61B 3/113
USPC .......................................................... 348/78
See application file for complete search history.

(56) References Cited

U.S. PATENT DOCUMENTS 6,293,674 B1    9/2001 Huang et al.
6,488,377 B2 *  12/2002 Matsumoto ............ A61B 3/145
                                                 351/206
8,414,564 B2 *  4/2013 Goldshleger .......... A61B 3/102
                                                 606/4
2009/0257636 A1  10/2009 Wei et al.
2011/0102742 A1   5/2011 Miyasa et al.
(Continued)

FOREIGN PATENT DOCUMENTS

JP    2009-517092 A    4/2009
JP    2010-200920 A    9/2010
(Continued)

OTHER PUBLICATIONS

International Search Report and Written Opinion issued for PCT/US2014/032184 dated Aug. 25, 2014, 10 pgs.
(Continued)

*Primary Examiner* — Brian Yenke
*Assistant Examiner* — Sihar Karwan
(74) *Attorney, Agent, or Firm* — S. Brannon Latimer

(57) ABSTRACT

A method to determine an ophthalmic tissue structure comprises measuring image data for a range of depths corresponding to a target point in an eye with an axial scanner with a probe; determining an image information by an imaging processor from the image data; identifying a tissue pathology corresponding to the target point by the processor from the image information; and signaling a user by a user indicator based on the identified tissue pathology. A corresponding apparatus comprises an axial scanner with a probe to measure image data for a range of depths corresponding to a target point in an eye; a processor to determine an image information from the image data, and to identify a tissue pathology corresponding to the target point from the image information; and a user indicator to signal a user based on the identified tissue pathology.

21 Claims, 6 Drawing Sheets

(56) References Cited

U.S. PATENT DOCUMENTS

| | | | |
|---|---|---|---|
| 2012/0274896 A1 | 11/2012 | Vermeer et al. | |
| 2012/0316545 A1 | 12/2012 | Blumenkranz et al. | |
| 2012/0316554 A1* | 12/2012 | Baron | A61B 18/08 606/34 |
| 2012/0330101 A1 | 12/2012 | Brennan et al. | |
| 2012/0330102 A1* | 12/2012 | Brennan | A61B 1/00096 600/177 |
| 2013/0058533 A1* | 3/2013 | Ren | A61B 1/00009 382/103 |

FOREIGN PATENT DOCUMENTS

| | | |
|---|---|---|
| JP | 2010-268916 A | 12/2010 |
| WO | 2006/022045 A1 | 3/2006 |
| WO | WO 2009/120543 | 10/2009 |

OTHER PUBLICATIONS

English comments and translation from Taiwan Search Report issued for Taiwan Application 103113024 dated May 21, 2015, 5 pgs.

Extended European Search Report issued in European Patent Application No. 14782137.5 dated Nov. 25, 2016, 8 pgs.

* cited by examiner

METHOD AND SYSTEM TO DETECT OPHTHALMIC TISSUE STRUCTURE AND PATHOLOGIES

BACKGROUND

Field of the Invention

An apparatus to determine a structure and pathology of an ophthalmic tissue described herein relates to imaging and image processing systems for ophthalmology. More particularly, the embodiments disclosed herein relate to the field of surgical procedures to treat retinal pathologies such as epiretinal membrane, macular holes, and macular pucker.

Description of Related Art

Epiretinal membrane (ERM) is a disease in which a layer of tissue grows on the interior surface of the retina. While there may be multiple causes for this pathology, it usually is a natural aging degeneration. As shown in FIG. 1, a retina 110 is composed of three main tissue layers: an internal limiting membrane (ILM) 111, in contact with vitreous gel 145 in the vitreous cavity 140, a nerve fiber layer (NFL) 112, and the optically sensitive neural layer. Retinal pigment epithelial cells are located (RPE) under the retina 113. Underlying the RPE layer is the choroid 115, which is a tissue containing blood vessels to provide oxygen and metabolic support to the RPE cells. Separating the RPE layer 113 and the choroid 115 is Bruch's membrane, allowing exchange of nutrients from the choroid 115 into the metabolically active RPE cells and waste material from the latter into the former.

As a result of the growth of an epiretinal membrane, the retina may become contracted or wrinkled in the macula area. The retina may become elevated away from the RPE causing damage to retinal function. These deformations result in defects of image formation at the macula, and need to be removed using a vitrectomy surgical procedure.

Vitreomacular traction is another pathological condition of the retina. Excessive adhesion between the vitreous and the ILM may result in the retina being elevated away from the RYE. As vitreous gel 145 moves anteriorly or is contracted, it may tear away portions of the inner surface of the retina into the vitreous chamber.

During surgical procedures to treat the above and other retinal pathologies it is necessary for the surgeon to distinguish between healthy portions of the retina and affected portions. The determination needs to be made in real time, as the surgeon proceeds with the intervention. Furthermore, the determination should require little involvement by the surgeon. The surgeon's attention should be focused on the physical procedure rather than analyzing ancillary information.

State-of-the-art methods to distinguish different tissue types involve the use of fluorescence techniques with differentiated markers. In a fluorescent marker approach, fluorophores emitting different colors of light are combined with suitable carriers that attach to a specific tissue. As a laser or other excitation light scans certain areas, the illumination spot turns into a different color, indicating the type of tissue being illuminated.

Unfortunately, the fluorescence approach may not be used for the treatment of retinal pathologies as described above. Typical fluorescent markers such as indocyanine green (ICG), trypan blue, and other stains have been used to stain ILM, with negative results. ICG is toxic and needs to be administered in low doses, and trypan blue produces weak stains that are difficult to see. Furthermore, there are no stains specific to ERM, and particulate marking of the vitreous humor, ERM, and ILM (e.g. using triamcinolone) is non-specific.

Other commonly used techniques may include tissue selective staining and observation with white light. ICG, Trypan blue, and Membrane Blue, are examples of some of the stains that may be used. The disadvantages of tissue staining are similar to those of fluorescence techniques mentioned above: toxicity to tissue (especially to sub-retinal tissues such as choroid 115) and the need to remove the dye after the procedure. Therefore, there is a need for a method and an apparatus to detect and determine tissue structure on an area to assess whether or not to perform a surgical procedure on that area. Also, a method is needed to detect tissue structure in real time without surgeon intervention to analyze data before making the determination.

SUMMARY

According to embodiments disclosed herein, a method to determine ophthalmic tissue structure comprises measuring image data for a range of depths corresponding to a target point in an eye with an axial scanner with a probe; determining an image information by an imaging processor from the image data; identifying a tissue pathology corresponding to the target point by the imaging processor from the image information; and signaling a user by a user indicator based on the identified tissue pathology.

According to embodiments disclosed herein, an apparatus to determine an ophthalmic tissue pathology comprises an axial scanner with a probe, configured to measure image data for a range of depths corresponding to a target point in an eye; an imaging processor, configured to determine an image information from the image data, and to identify a tissue pathology corresponding to the target point from the image information; and a user indicator configured to signal a user based on the identified tissue pathology.

These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

Figure 1:
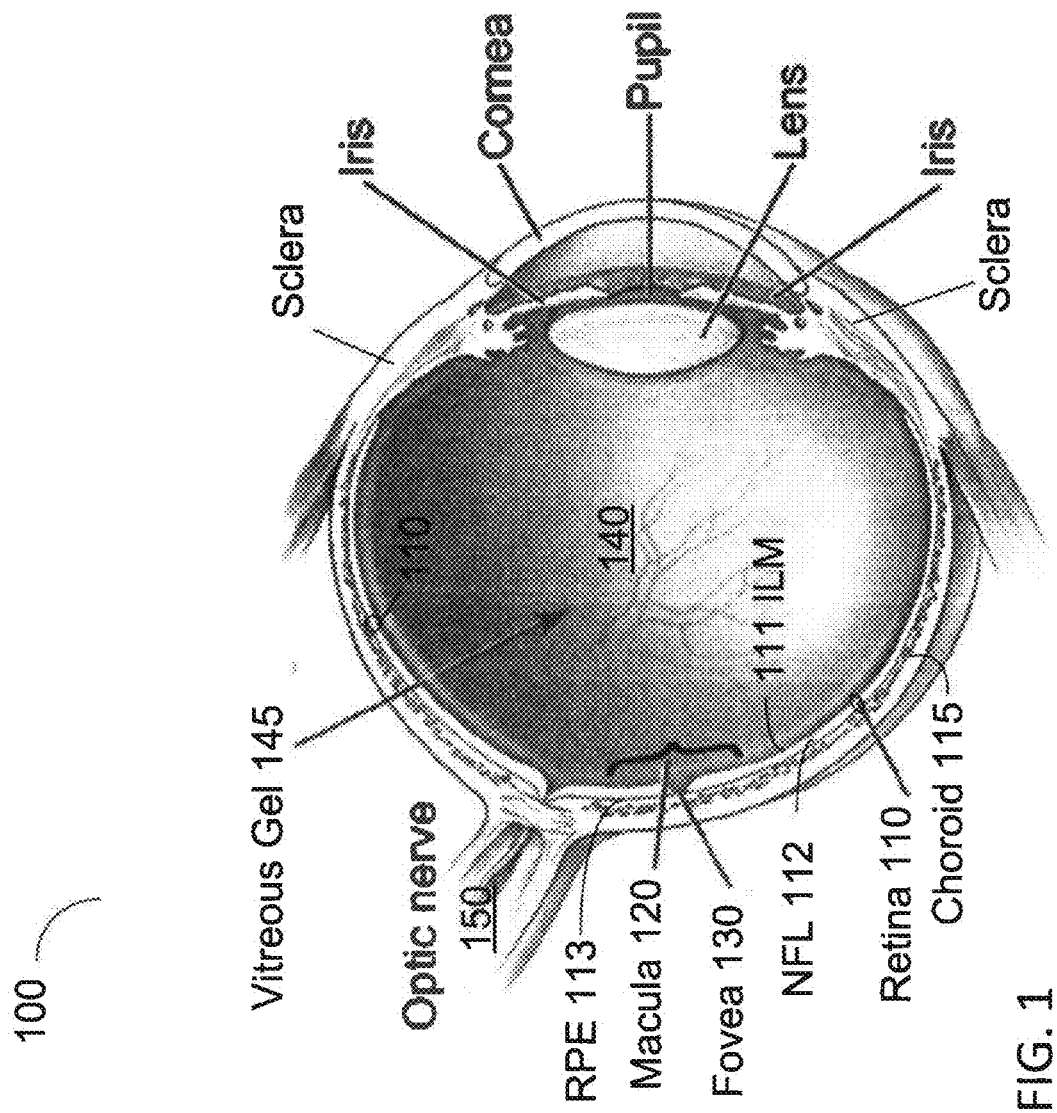
FIG. 1 shows a schematic view of the human eye including the retina, the optic nerve, and the vitreous gel.

FIG. 1 shows a schematic view of the human eye 100, including retina 110, optic nerve 150, and vitreous gel 145, as they are relevant for embodiments disclosed herein. Portions of eye 100 located in the front, such as the iris, the cornea, the sclera, the pupil, and the lens are also shown in FIG. 1 for completeness. Vitreous gel 145 is the material filling vitreous cavity 140, which is limited in the back portion by retina 110. Macula 120 is a portion of retina 110 having a center at fovea 130, where the central vision is collected. The lens creates an image that is centered on macula 120. Retinal tissue layers such as ILM 111, NFL 112, and RPE 113, are also illustrated in FIG. 1 and have been described above.

The lens creates an image that is centered on fovea 130, covering macula 120 and other parts of retina 110. Optical rays traverse NFL 112 and reach RPE 113 where they excite photosensitive cells that generate stimulus pulses. The stimulus pulses from RPE 113 are transmitted by NFL 112 to optic nerve 150, which in turn transmits the signal to the brain, where an image is created.

Figure 2:
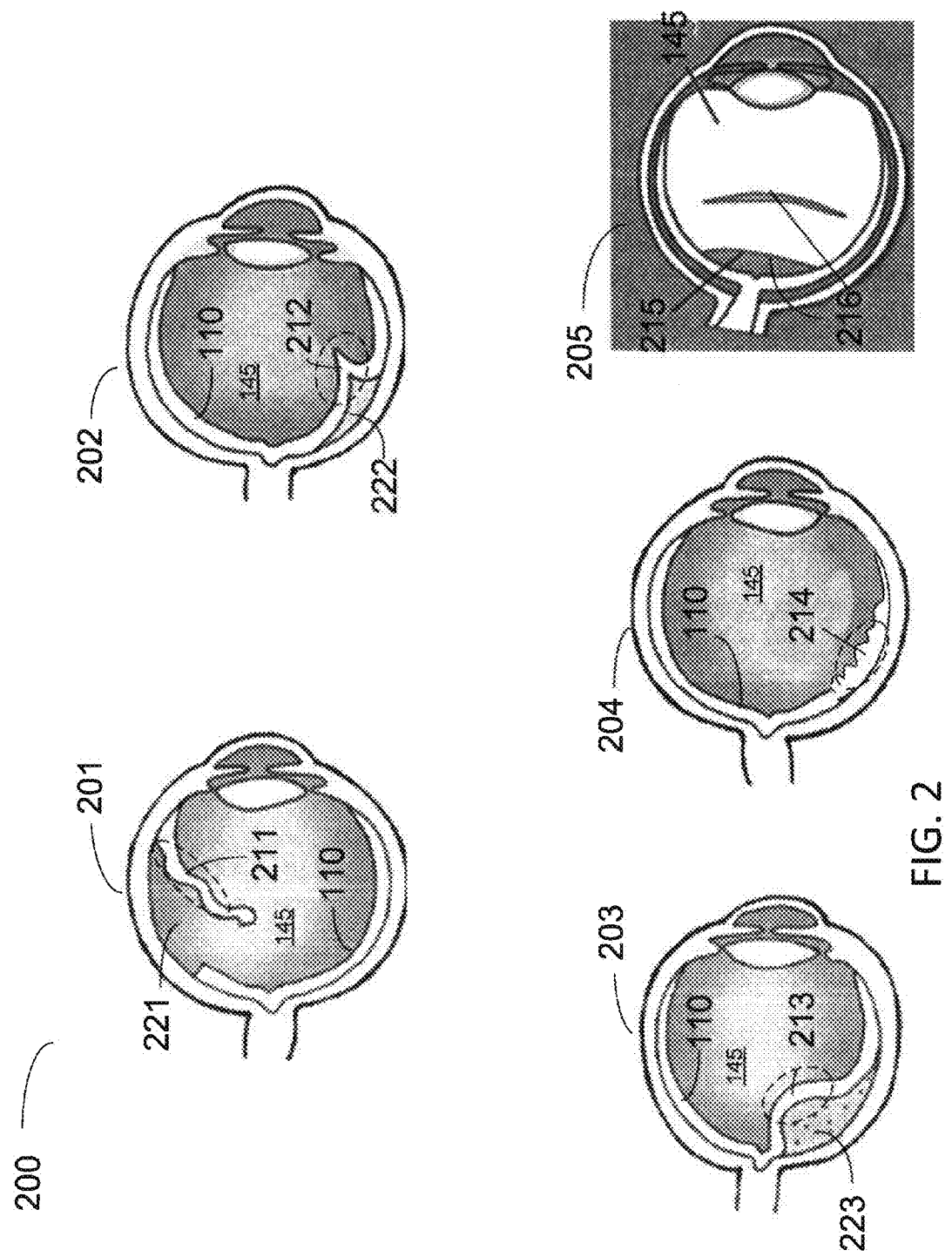
FIG. 2 shows a schematic view of pathologies and corresponding retinal structures to be treated using a method according to some embodiments.

FIG. 2 shows a schematic view of pathologies 201-205 with retinal structures 211-215 to be treated using a method according to some embodiments. A detailed description of each tissue structure 201-205 follows.

Rheghmatogenous retinal detachment 201 is a common form of ERM where a full-thickness portion 211 of retina 110 detaches and dangles into vitreous chamber 140. A portion of vitreous gel 221 moves underneath detached retinal portion 211.

Vitreous traction 202 has been described in the background section. In a traction event 202, a portion of the retina 110 is pulled from its base by vitreous gel 145, creating a cusp-like structure 212. Underneath detached portion 212, material 222 including vitreous gel, hemorrhagic blood and inflammatory cells moves into place.

Retinal detachment 203 may be provoked by hemorrhagic or exudative events where blood or fluid 223 builds up under retina 110, creating a hump-like structure 213. Macular puckering 204 occurs when cells in retina 110 become stressed, e.g. due to an immune system response. The tension generated due to convergence of immune cells on the tissue may cause retina 110 to pucker and form a wrinkled portion. 214. A retinal pucker may occur anywhere in the retina, including macula 120. Macular pucker is optimally referred to as epimacular membrane.

Posterior vitreous detachment (also known as vitreous cortex) 205 is the consequence of liquefaction of vitreous gel 145. This process is typically the result of aging. Vitreous gel 145 may contract forming a cortex 215, leaving behind liquid portions 216 that may need to be removed. The vitreous contraction and the liquid 216 may induce a small tear in retinal tissue, leading to a macular hole (see below).

Other retinal pathologies may be consistent in general with the five structures 211-215 shown in FIG. 2. Embodiments of the methods, procedures, and apparatus disclosed herein are not limited to the pathologies depicted in FIG. 2, as other pathologies may be well known to those skilled in the art of ophthalmic surgery.

Some embodiments of the methods, procedures and apparatus disclosed herein may be used in surgical tasks such as finding retinal rupture points and other disruptions, or as a general surgical tool to e.g. locate retina-attached vitreous gel that may remain in the retina after an extraction procedure.

Some embodiments of the methods, procedures and apparatus disclosed herein may be used in the treatment of sub-retinal pathologies, e.g. pathologies affecting the choroid 115 and sclera. Another retinal pathology that may be treated using methods, procedures and an apparatus consistent with this disclosure may be macular hole. Macular hole is the result of vitreous traction in macula 120.

When a surgeon intervenes in a patient for any of the pathologies depicted in FIG. 2, precise knowledge of the nature of the structure at the point of intervention is desirable. As the intervention proceeds, information about the underlying structure needs to be updated without hindering the progress of the procedure.

Figure 3:
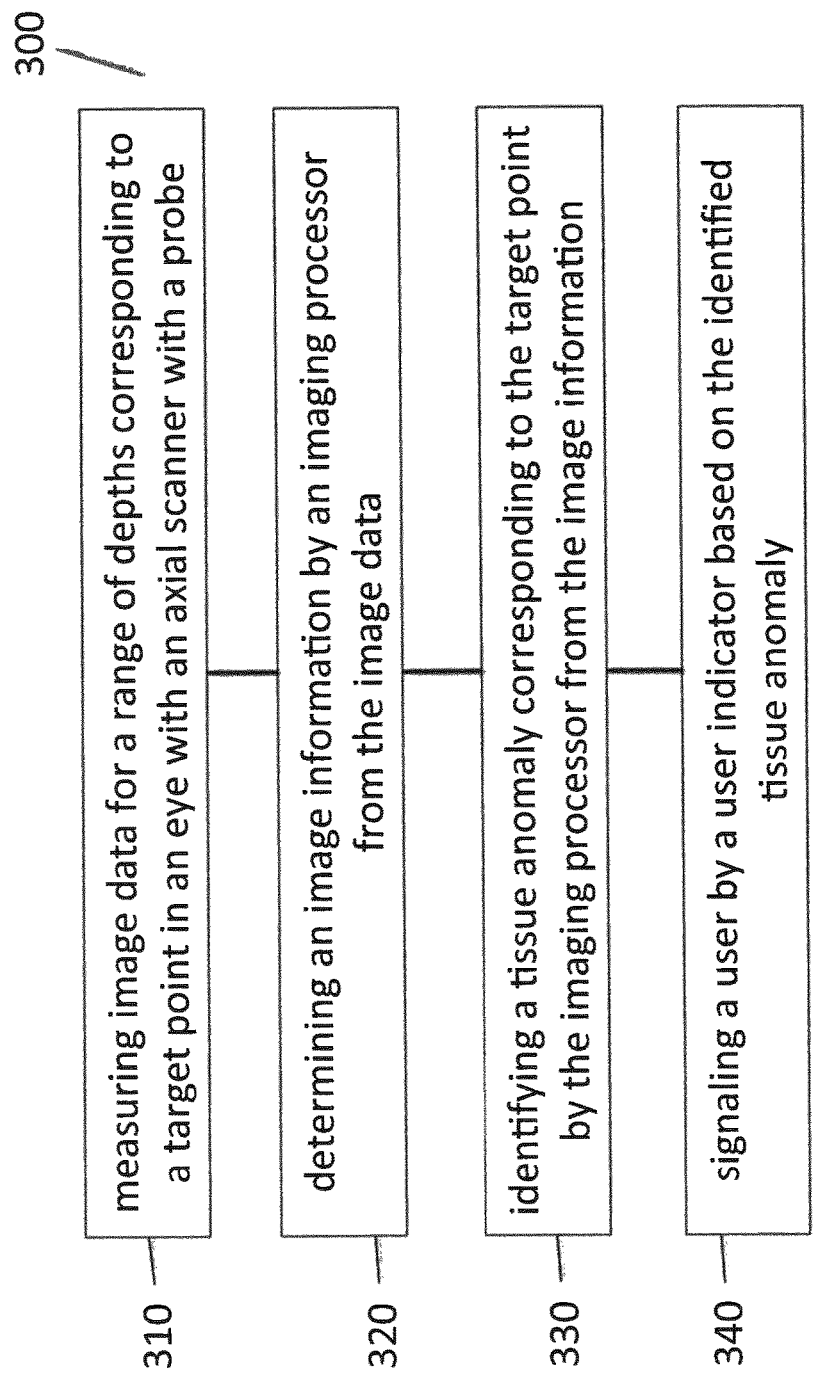
FIG. 3 shows a flow chart of a method to detect tissue structure using an axial scanner with a probe, according to some embodiments.

FIG. 3 shows a flow chart of method 300 to determine an ophthalmic tissue structure, the method comprising the following steps. Step 310 can involve measuring image data for a range of depths corresponding to a target point in an eye with an axial scanner with a probe. Step 320 can involve determining an image information by the imaging processor from the image data. In step 330, identifying a tissue pathology, structure, or anomaly corresponding to the target point by the imaging processor from the image information can be performed. Finally, step 340 can involve signaling a user by a user indicator based on the identified tissue pathology. These steps will now be described in detail.

In step 310, image data can be measured by an Optical Coherence Tomography (OCT) imaging system or by any other type of axial scanner. OCT imaging systems and axial scanners are configured to gather imaging data corresponding to a target point for a range of depths. Correspondingly, an OCT or an axial scanner imaging system can image the target tissue over the range of depth.

An OCT imaging system can include a laser source to generate an imaging beam and an optical cable to deliver the imaging beam towards an imaging probe. The imaging probe can be inserted into the eye to be positioned close to the target point, such as to a point of the retina. In some embodiments, the imaging probe can even be brought into contact with the retina, or at least positioned in close proximity to the retina. The target point may be a spot on the retina where the surgeon is plans to perform an ophthalmic surgical procedure. The imaging probe can project or focus an imaging beam onto the target point and then receive a returned of reflected beam, reflected from a range of depths corresponding to the target point.

The returned imaging beam can be delivered back to a detector of the OCT imaging system, where it can be interfered with a reference beam by a beam splitter to generate an interference beam. Processing the interference beam by the detector decodes image data related to the range of depths corresponding to the target point, all of it coded in the phase of the returned imaging beam. This processing can be performed by a scanning processor of the axial scanner, such as a scanning processor of the OCT imaging system.

Figure 5:
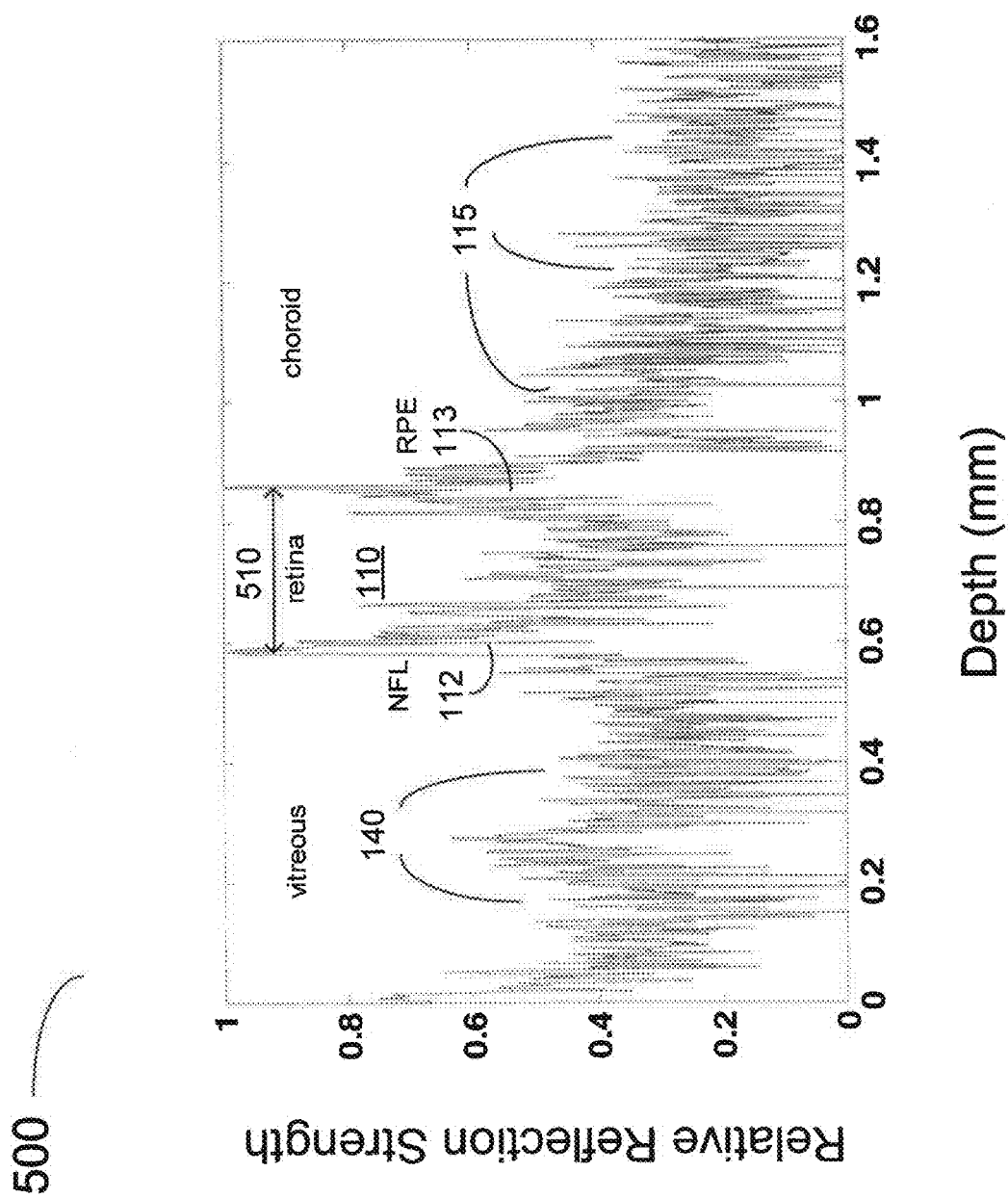
FIG. 5 shows a partial view of a one-axis OCT A-scan of a healthy retina, according to some embodiments.

In some embodiments, the image data can be not only a reflection strength, but also a scattering amplitude, an absorptivity, a noise, a fluctuation, and an optical data, corresponding to the range of depth of the target tissue. FIG. 5 illustrates an example of imaging data: in this embodiment the imaging data is a relative reflection strength, measured in a range of depths of about 1.6 mm. This embodiment of the OCT imaging system has a high resolution, and thus measures the relative reflection strength at a very large number of depths within the depth range. OCT imaging systems can have a resolution of a few microns, thus in a depth range of a millimeter, they can determine the reflection strength at several hundreds or even at a thousand depths or depth points. Such a depth-scan, or axial scan, is often called an A-scan. In embodiments, the measuring image data can be performed without using fluorescent markers.

Step 320 can involve transferring the image data from the axial scanner to the imaging processor. In some embodiments, this can involve transferring the set of numerical values of the reflectivity at the large number of depths corresponding to the target point on the retina, such as the image data in FIG. 5. In some embodiments, this imaging processor can be different from the scanning processor of the axial scanner, as described in relation to FIG. 6 below. In other designs, the functions of the scanning processor and the imaging processor can be performed by the same processor of a computer. In such designs, step 320 need not involve a transferring operation.

Step 320 can include determining image information by the imaging processor from the image data. The determining of image information can include identifying two or more image features, wherein an image feature can be one of a peak, valley, maximum, minimum, halfway point, transition point, and plateau of the image data as a function of depth.

In the example of FIG. 5, the imaging processor can use a search algorithm to determine local maxima of the relative reflection strength. For some retinal layers, detailed in relation to FIG. 1, their interfaces and boundaries scatter and reflect light stronger than their internal portions, the depth, or location of these layer-boundaries can be identified by identifying the local maxima of the reflectivity. In the case of some retinal layers, the entire layer can scatter or reflect the imaging light stronger than its neighboring layers. These layers can cause not only a local maximum, but a plateau, or sustained enhanced region in the image data, such as the reflectivity.

FIG. 5 illustrates that the boundaries of retina 110 can be identified as local maxima of the relative reflection strength, located at depths of about 0.6 mm (600 microns) and at about 0.85 mm (850 microns). In the proximal region of retina 110, NFL 112 can be identified from the elevated reflectivities, and in the distal region of retina 110, RPE 113 can be identified from the elevated levels of the reflectivity.

Given the noisy nature of the image data, identifying the image features, such as maxima, minima, or plateaus can involve using mathematical techniques, such as an averaging, a smoothing, a linear regression technique, a spectral decomposition technique, a low-pass filter, a fitting procedure, or equivalents.

Step 320 can include determining not only the existence of image features, but also recording their depths. This can be followed by measuring or determining a depth difference between two of the identified image features. This depth difference can be part of the image information. The depth difference between the two outer surfaces of retina 110 is a measure of the thickness of retina 110. In the example of FIG. 5, this depth difference d can be measured to be about d=0.85 mm−0.6 mm=0.25 mm (250 microns), as discussed below in more detail.

Since this process involves comparing the depths of different image features, the imaging processor can perform step 320 in conjunction with an imaging memory circuit, where some of the image data and the corresponding depths are stored.

Step 330 can include identifying a tissue pathology or anomaly that can involve determining an existence of the tissue pathology or determining a thickness of the tissue pathology based on the image information, or both. The tissue pathology or anomaly can be determined from the image information that includes the depth difference of image features and thus the information about the thickness of target layers, such as a retinal layer or the entire retina. In other embodiments, the tissue pathology or anomaly can be determined from the anomalous depths of the ophthalmic layers.

As discussed in relation to FIG. 1, several retinal diseases are accompanied by an anomalously increased retinal thickness. To recognize such retinal pathologies, the imaging processor can use the determined retinal thickness and perform a comparison to other relevant thicknesses. For example, the operation of the axial scanner can involve moving the scanning probe along a scanning line, recording the retinal thicknesses along the line in a memory circuit, comparing the thicknesses along the line by the imaging processor, and signaling if the thickness at a particular location or in a particular segment of the line is thicker or thinner than at others. Such a thickness anomaly can indicate a retinal disease.

Other retinal diseases or pathologies can be recognized from the retina's distal boundary surface exhibiting a depth different from the depth of proximal surface of the underlying supporting layer choroid 115, signaling a retinal detachment. In yet other retinal diseases, the average retinal thickness may not be that different form a typical value, but the thickness may exhibit larger than usual spatial variations, indicating an anomalous unevenness of the retina. These are examples that the image information can be other than only a layer thickness.

FIG. 5 illustrates the steps 310, 320 and 330 in more detail. FIG. 5 shows a partial view of A-scan 500 from retina 110, according to some embodiments of method 300. Scan 500 corresponds to the section labeled AA' in FIG. 4, located at a lateral position of approximately 0.6 mm. Scan 500 displays the result of step 310, the measurement of image data, in this case that of the relative reflectivity strength at a large number of depths within a depth segment 0-1.6 mm of the eye along an axial or Z-direction. The vitreous cavity 140 and the choroid 115 reflect only to a limited degree and therefore appear as regions with reduced reflectivity in scan 500. Two peaks appear in the image data, corresponding to NFL 112 and RPE 113. The space between a proximal surface of NFL 112 and a distal surface of RPE 113 is retina 110, with thickness 510.

In step 320, the image features can be located by the imaging processor by performing an algorithm that searches the local maxima or other image features of the image data. Examples of the algorithm can include an averaging, a smoothing, a linear regression technique, a spectral decomposition technique, a low-pass filter, a fitting procedure, or equivalents.

In FIG. 5 the image features include the two peaks and the corresponding depths. Thus, the imaging processor can determine the location of the proximal and the distal boundary surfaces of retina 110. Still within step 320, in some embodiments, the imaging processor can determine a depth difference of two image features, such as a depth difference of the two boundary surfaces. This difference is a reliable measure of the thickness 510 of retina 110.

The knowledge of the location of the retinal boundaries and the retinal thickness allows in step 330 the imaging processor to determine the status of retinal tissue 110 at point A and to identify whether the retinal tissue exhibits a pathology or anomaly. Several tissue pathologies and the corresponding embodiments of step 330 will be discussed next.

For example, in certain conditions such as in the macular puckering 204 of FIG. 2, thickness 510 may be larger than a certain standard or threshold. Thus, in step 330 the determination of the image information that the retinal thickness exceeds a normal value, or is outside a normal range, can be interpreted as evidence for macular puckering. In other situations, enhanced thickness 510 may indicate an inflammation of retina 110 at point A.

In the case of retinal detachment such as 201-203 in FIG. 2, the image information gleaned from A-scan 500 may show excess materials 221-223 being present under detached retina 211-213. Because blood and fluids in excess materials 221-223 may have a different reflectivity than choroid 115, excess materials 221-223 may have a different reflectivity level in A-scan 500 than the valleys of vitreous gel 145 and choroid 115.

In the macular puckering 204 of FIG. 2, a collection of A-scans taken at points of interest relatively close to one another may show a thickness 510 of retina 110 changing drastically between different points: another type of indication of a tissue pathology.

Yet another type of tissue pathology is connected to the posterior vitreous detachment 205 of FIG. 2. An A-scan 500 may provide indication of the presence of ILM 111, epiretinal membrane 214, and detached vitreous cortex 215. Additionally, anomalous tissue 216 can also be present that can be either a fully detached portion of the retina, or in some cases, vitreous gel 145.

In all of these embodiments, image data in A-scan 500 can exhibit image features, such as local maxima, elevated plateaus, sharp minima or valleys. The imaging processor can be configured to identify any and all of these image features and the corresponding depth values. Finally, the imaging processor can extract additional characteristics, such as the depth-difference or distance of image features that can be indicative of tissue thicknesses, or tissue detachments. The identification of the image features, their depths and the depth differences together can be part of the image information, determined by the imaging processor in step 320. Based on these image information, in step 330 tissue pathologies can be determined, by the imaging processor. The imaging processor can evaluate tissue pathologies based on communicating with a lookup table that stores the correlation between image information and the various retinal pathologies.

Of the above-discussed embodiments, many involved measuring and analyzing a single A-scan. However, the efficiency of method 330 to recognize tissue pathologies can be enhanced by comparing the depth of the target tissue at a particular surface point to the depths at other surface points of the target tissue. To improve the efficiency by such multiple imaging procedures, method 300 can involve scanning the probe along a scanning line over the target region and performing A-scans at a set of points along the scanning line. A set of image data, corresponding to the sequence of target points, can be assembled by the scanning processor.

Figure 4:
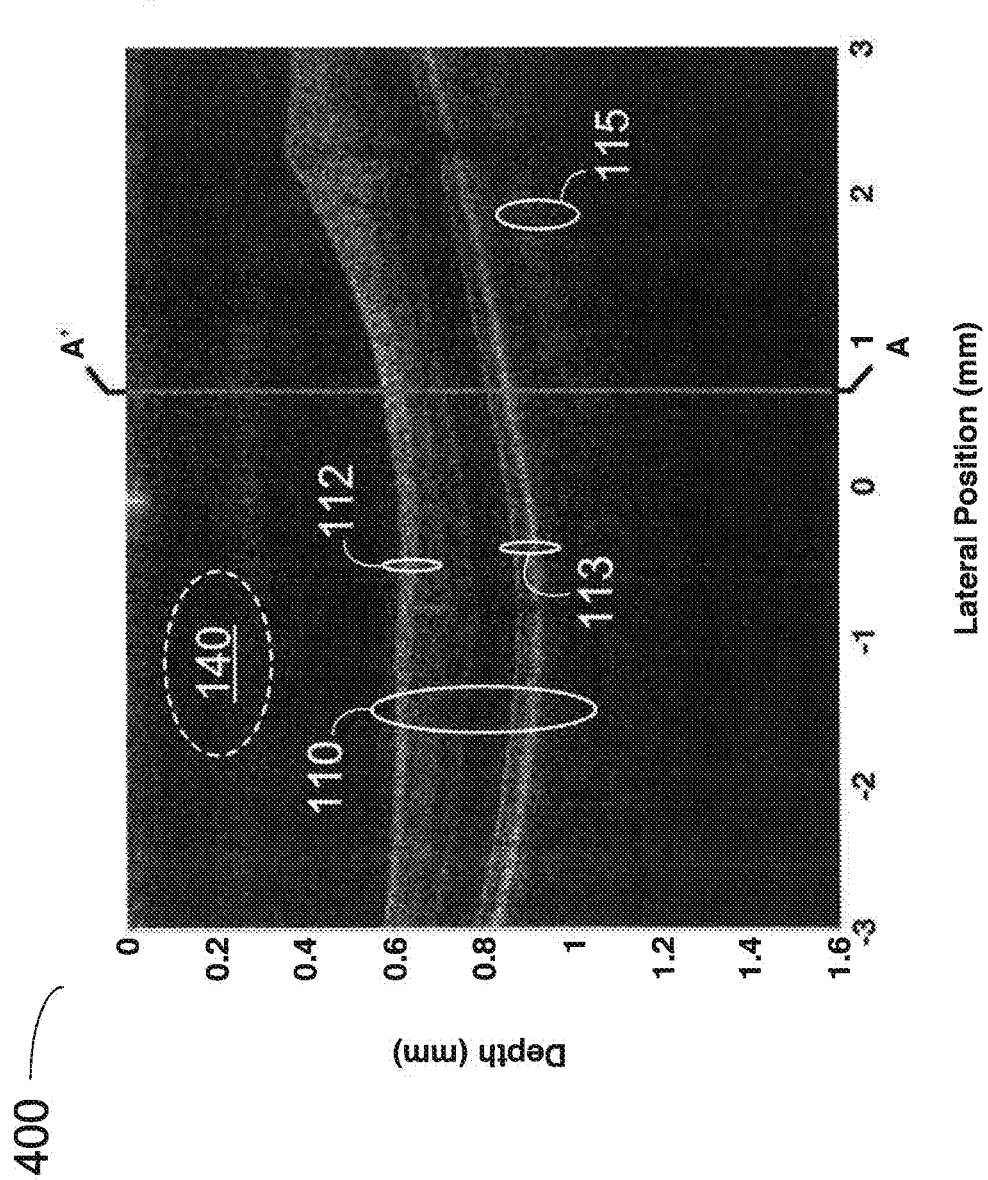
FIG. 4 shows a partial view of an OCT B-scan of a retina, according to some embodiments.

FIG. 4 illustrates such an assembly of A-scans, typically referred to as a B-scan. In the B-scan shown, the reflectivity is indicated by a grey scale. For example, a sharp variation of the grey scale in a B-scan can indicate the tissue boundary. It is noted here that the terms "A-scan" and the "scanning of a depth segment" refer to gathering image data along a Z-axis of the imaging system at a fixed target point on the tissue surface. On the other hand, scanning in the context of the B-scan refers to a lateral scan of the probe and imaging beam, scanning the target point itself along the tissue surface, as the context makes it clear.

Once the imaging system creates a B-scan, the imaging processor can identify the image information and based on that, the tissue pathology by comparing the image information along the sequence of target points. Analogously to the A-scans, the imaging processor can use various mathematical techniques for this analysis, including averaging image information along the sequence of target points, filtering image information along the sequence of target points with a Kalman filter, using a linear regression technique, using a principal components analysis technique, and using a lookup table correlating at least one image information to at least one tissue pathology or tissue structure. Since the imaging processor is comparing image data and image information from sequentially taken A-scans, the imaging processor or the imaging system can include a memory circuit that can store the image data and image information of A-scans.

FIG. 4 shows a partial view of B-scan 400, generated by assembling a large number of A-scans, taken by an OCT technique on a healthy retina 110, according to some embodiments. FIG. 4 corresponds to a sagittal view of retinal tissue. B-scan 400 shows retina 110, vitreous cavity 140, and choroid 115. A multilayered structure of retina 110 is evident in B-scan 400. The upper or proximal layer includes NFL 112, and the lower or distal layer includes RPE 113. While other structures may be apparent in B-scan 400, NFL 112 and RPE 113 are easily distinguishable because they provide the highest reflectivity in retina 110. In fact, NFL 112 and RPE 113 provide the highest reflectivity in the entire field shown in B-scan 400. This high reflectivity was shown also in the elevated values of reflectivity in FIG. 5.

In embodiments of the method 300 the probe of the axial scanner, such as the OCT imaging scanner, can be inserted into the eye before measuring image data. This feature, the insertable probe, can force requirements on the imaging system that are considerably more stringent than the requirements of ophthalmic imaging systems that are used only externally. Probes can be inserted only in a surgical environment, whereas external probes can be operated in an outpatient office, such as in a diagnostic environment.

The signaling in step 340 can include providing a visual or non-visual signal to the user of the system, such as the surgeon. The user indicator may provide a blinking of a light beam aimed at the target point on the retina to signal the tissue pathology or structure. Thus, in step 340 the user indicator may indicate the tissue pathology determined in step 330 by projecting a visual signal on the retina itself. For example, blinking once may indicate the presence of only ILM 111 (healthy retina). Blinking twice may indicate the presence of epiretinal membrane or puckering 214, and blinking three times may indicate the presence of detached vitreous cortex 215. Providing these signals without forcing the surgeon to look away from the surgical microscope makes the job of the surgeon much easier: the surgeon can concentrate on performing the scanning imaging of the target tissue with the probe and will not be forced to repeatedly turn away from the surgical microscope and analyze complex images for pathologies.

In other embodiments, the imaging system can display a heads-up signal in the surgical microscope. In yet other embodiments, the blinking of an aiming or sensing optical beam may be replaced or complemented by an audible beep. A single beep may indicate ILM 111 only, two beeps may indicate membrane 214, and three beeps may indicate detached cortex 215. Other embodiments consistent with FIGS. 3-5 may include the use of other non-imaging or non-optical indicators for the tissue structure or pathology. These embodiments, a surgeon is made aware of whether there is ILM 111, epiretinal membrane 214, or detached vitreous cortex 215 without the need to interpret a complex image.

Some embodiments of the methods, procedures and apparatus disclosed herein may include the removal of waste material from retinal layers such as RPE 113. Waste materials such as lipofuscin tend to be highly toxic, and photosensitive. Thus, photocoagulation techniques as described above may be used to remove such materials, according to methods consistent with FIGS. 3-5. For example, an OCT A-scan 500 may be used to determine the presence of lipofuscin material at a target point. In step 340, a signal from an user indicator can prompt either a surgeon or an automatic mechanism to make an operational decision, such as providing a certain dosage of light to the target point.

In this example, if the lipofuscin is not present or is present at a level below a certain threshold, a new point of interest may then be selected. Analogously, in most embodiments, if no tissue pathology has been detected in steps 310-330, then the user indicator can provide a signal for the surgeon or for an automated controller to move the scanning probe to a new point.

Figure 6:
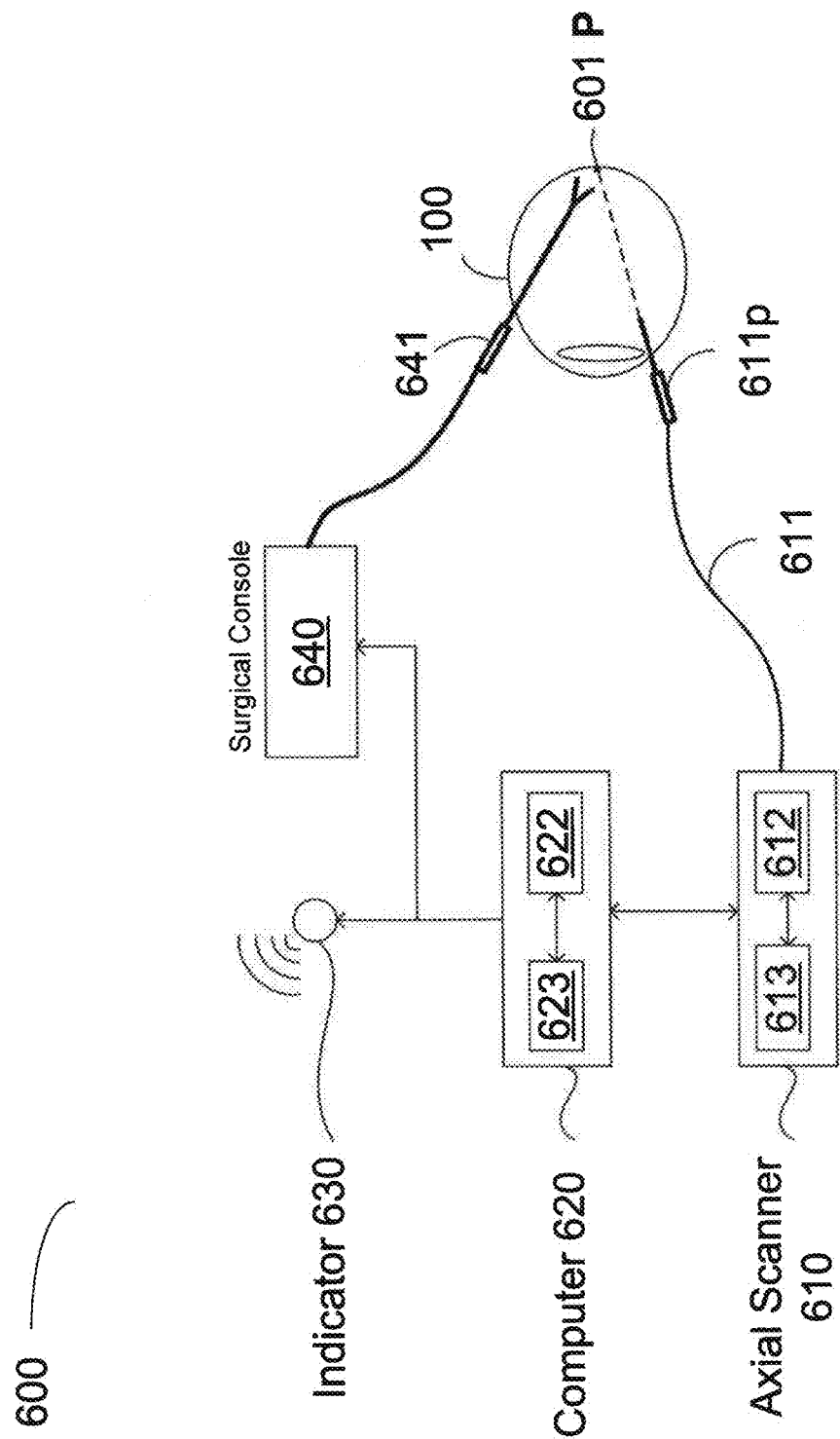
FIG. 6 shows a system to detect tissue structure in ophthalmic surgery according to some embodiments.

FIG. 6 shows an embodiment of an imaging system 600 to detect a tissue pathology or anomaly in ophthalmic surgery according to some embodiments. According to FIG. 6, imaging system 600 may be configured to determine an ophthalmic tissue pathology or anomaly and may include an axial scanner 610 with a probe 611 to measure image data for a range of depths corresponding to a target point P 601 in an eye. Imaging system 600 may further include an imaging computer 620 with an imaging processor 622 to determine an image information from the image data and to identify a tissue pathology corresponding to the target point P 601 from the image information; and a user indicator 630 to signal a user based on the identified tissue pathology. Some embodiments can also include surgical console 640.

Scanner 610 can include imaging probe 611, scanning processor 612, and memory circuit 613. In some embodiments of system 600, probe 611 is an optical probe providing a beam of light directed to P 601 through a line of sight (LOS). LOS is shown as a dashed line from distal portion 611p of probe 611 to target point P 601. The optical cable and distal portion 611p of probe 611 can guide an imaging light from scanner 610 to the target point P 601. Distal portion 611p also receives the returned imaging light, reflected by the tissue at the target point P 601. Probe 611 carries back the returned imaging light a signal providing image data from P 601. In some embodiments, portion 611p may be inserted inside eye 100. In other embodiments, probe 611 may provide illumination light through the cornea, without being inserted into the eye.

The returned imaging beam from probe 611 can be analyzed by scanning processor 612 and stored in memory circuit 613. Memory circuit 613 may also store image data corresponding to target points the probe portion 611p was directed at before it was directed to P 601. As before, the image data can include the reflectivity of the target tissue in a range of depth and the corresponding depth values. The image data can also include the lateral position of the imaging probe's distal portion 611p, as it was shown in FIG. 4. Scanning processor 612 may perform operations on the image data extracted from returned imaging beam, such as noise filtering, averaging, and calibrating with a reference value.

The length of portion 611p may be 3-4 inches (approximately 7.5 cm to 10 cm), or more. Portion 611p may have a broader part or hand-piece to be handled by a surgeon, and a tip or narrow end in its distal portion. The broad part or hand-piece in portion 611p may be about 8 mm to about 18 mm in diameter, and between 45 mm and 90 mm in length. In some embodiments the tip may be approximately 25 to 35 mm in length and have a diameter between 20 gauge and 25 gauge, or less than about 1 mm to about 0.5 mm. Some embodiments of probe 611 may include portion 611p being smaller than 25 gauge, such as 27 gauge or even smaller. In some embodiments the diameter of portion 611p may be as low as 50 gauge. Probe 611p may be an endoprobe in which the distal end is inserted into the eye 100, according to some embodiments. In other embodiments, probe 611p may be outside the eye 100, illuminating point P 601 through the cornea.

Scanner 610 can be coupled to imaging computer 620 and provide imaging computer 620 the image data generated by scanning processor 612. Imaging computer 620 can include imaging processor 622 and memory circuit 623. According to some embodiments of system 600, imaging computer 620 and scanner 610 may be integrated into a single unit. In such cases, scanning processor 612 and imaging processor 622 may be the same processor circuit, or different portions of the same processor circuit. Also, memory circuits 613 and 623 may be the same circuit, or different portions of the same memory circuit. Memory circuit 623 may store information regarding a set of points P 601, and imaging processor 622 may perform calculations using this information.

In some embodiment of system 600 the imaging processor 622 can identify two or more image features, wherein an image feature is one of a peak, valley, maximum, minimum, halfway point, transition point, and plateau of the image data as a function of depth; and measure a depth difference between two of the identified image features, wherein the depth difference is part of the image information.

The imaging processor 622 can be able to identify the tissue pathology by averaging image information along the sequence of target points, filtering image information along the sequence of target points with a Kalman filter, using a linear regression technique, using a principal components analysis technique or using a lookup table correlating at least one image information to at least one tissue structure.

For example, imaging processor 622 may perform data smoothing operations in order to remove transient fluctuations in the signal. In some embodiments, such smoothing operations may include averaging signals produced by the set of points P 601. Other embodiments may include the use of frequency filters and windows for data processing in imaging processor 622. Further embodiments may include the use of a Kalman filter having a predictor value and a standard deviation from the predictor value.

Based on a determination of tissue pathology or structure at P 601 in step 330, imaging computer 620 can provide a signal to user indicator 630. User indicator 630 can communicate the tissue pathology information to the surgeon or technician performing the surgical intervention. User indicator 630 may be a laser or light source providing visible light through the optical path of probe 611 to illuminate the target point with light having a certain color. As mentioned above the visible light of indicator 630 may include a light beam having a visible color, such as red, green, or blue. Thus, once an image information is used by imaging processor 622 to determine a tissue pathology, imaging computer 620 can signal user indicator 630 to use a light source having a pre-selected color and provide an indicator beam through the optical path of probe 611 to indicate for the user of the imaging system 600 the determined tissue pathology or anomaly. As discussed above, the indication can be a visual or non-visual signal, and can be such that it does not force the surgeon to look away from the surgical microscope.

Some embodiments of system. 600 may further include a surgical microscope providing a view of the target point P 601 during the intervention. In these embodiments, the user indicator 630 may be a visual indicator as described above, coupled to the distal end of probe 611p. In such embodiments, the signal provided by the user indicator 630 may be projected onto the target tissue and into the view of the surgical microscope.

According to embodiments of system 600, imaging computer 620 may be coupled to a surgical console 640, and can provide the tissue pathology determination to surgical console 640. Surgical console 640 can include mechanical devices and systems to perform the ophthalmic surgical intervention on eye 100. Some embodiments may include surgical actuator 641 having a tip in the distal end, to perform the intervention. For example, actuator 641 may include a pair of scissors at the distal end. Other uses, procedures, and components of surgical console 640 to perform ophthalmic surgery may be evident to one of regular skill in the art. Corresponding ophthalmic surgical components can be included herein in embodiments of system 600 consistent with the concept illustrated in FIG. 6.

In some embodiments of system 600 as illustrated in FIG. 6, the tissue structure or pathology determination provided by imaging computer 620 may be used by surgical console 640. Surgical console 640 may update its configuration status based on the tissue anomaly determination at P 601. For example, if it is determined that the structure at P 601 corresponds to one of the pathologies 201-205 of FIG. 2, then console 640 may enable surgical actuator 641 and prepare the tip for an intervention. This may include powering up the teed mechanism for a pair of scissors, such as a pneumatic scissor system. Thus, while the ultimate command can still be provided by the surgeon, system 600 may get console 640 ready to perform the intervention. Embodiments of system 600 using this approach can provide a smooth and quick pace for ophthalmic surgery, enabling the surgeon to concentrate on the intervention itself. Also, embodiments of system 600 can provide the surgeon with extra time prior to performing the intervention at each point P 601, review the procedure, and think ahead of the next surgical steps.

In some embodiments consistent with FIGS. 3-6, collecting a B-scan from a plurality of A-scans may include the use of a gyroscope and an accelerometer to track the trajectory of axial scanner with a probe 610 (such as an OCT scanner) along different points of interest 601. Other means for tracking axial scanner 610 with a probe 611 may include the use of a magnetic sensor to track the motion of probe portion 611p. In some embodiments, a gyroscope, an accelerometer, and a magnetic sensor may be included in axial scanner with a probe 610, having a sensor coupled to portion 611p. In some embodiments, a gyroscope, an accelerometer, and a magnetic sensor may be controlled automatically from surgical console 640. Some embodiments may use a surgical microscope as described above for tracking the motion of probe portion 611p from one point 601 to the next. The surgical microscope may provide a digital image to a processor such as 612 or 622, or to a controller included in console 640. The digital image may be processed to determine precisely the location of target point P 601 within eye 100. Thus, a B-scan may be formed from a collection of precisely tracked A-scans.

More generally, the tracking methods and devices described above (e.g., gyroscope, accelerometer, and magnetic sensors) may be used to track the movement of probe portion 611p along a trajectory in a plane substantially perpendicular to the axial scan. In some embodiments, the motion of probe portion 611p along such a trajectory may be complemented with the motion of an optical beam coming out of probe portion 611p. For example, an optical beam forming the LOS depicted by a dashed line in FIG. 6 may describe a trajectory for point 601 in a plane substantially perpendicular to the axial scan, or to the axis of portion 611p, according to some embodiments.

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

The invention claimed is:

1. A method to determine an ophthalmic tissue structure, the method comprising:
   inserting a physical probe of an axial scanner into an eye;
   moving the probe along a scanning line while measuring image data for a range of depths corresponding to a retinal target point in an eye with the axial scanner;
   determining, by an imaging processor coupled to a memory, an image information from the image data, including identifying two more image features in the image data that represent boundaries of retinal tissue layers along the scanning line;
   identifying, by the imaging processor coupled to the memory, a retinal tissue pathology corresponding to the target point by comparing the two or more image features representing boundaries of tissue layers at a first portion of the scanning line to the two or more image features representing boundaries of tissue layers at a different, second portion of the scanning line;
   based on the identified retinal tissue pathology, determining a type of the retinal tissue pathology based on retinal pathology data stored in the memory;
   generating, by the imaging processor coupled to the memory, a signal to indicate to a user the type of the retinal tissue pathology, wherein the signal comprises a change to a characteristic of a light beam visible in a surgical field that corresponds to the type of the retinal tissue pathology.

2. The method of claim 1, wherein:
   the image data is one of a reflection strength, a scattering amplitude, an absorptivity, a noise, a fluctuation, and an optical data.

3. The method of claim 1,
   wherein at least one of the image features is one of a peak, valley, maximum, minimum, halfway point, transition point, and plateau of the image data as a function of depth; and
   wherein the determining of an image information comprises:
   measuring a depth difference between two of the identified image features, wherein the depth difference is part of the image information.

4. The method of claim 1, the identifying the tissue pathology comprising:
   determining at least one of an existence of the tissue pathology and a thickness of the tissue pathology based on the image information.

5. The method of claim 1, wherein identifying the tissue pathology comprises assembling a set of image information corresponding to a sequence of target points by the imaging processor; and
   determining the type of the tissue pathology comprises comparing the image information along the sequence of target points with the retinal pathology data stored in the memory.

6. The method of claim 5, the determining the type of the tissue pathology comprising at least one of:

averaging image information along the sequence of target points,
filtering image information along the sequence of target points with a Kalman filter,
using a linear regression technique,
using a principal components analysis technique, and
using a lookup table correlating at least one image information to at least one tissue structure.

7. The method of claim 1, comprising:
storing the image data and at least one configuration parameter from the axial scanner in the memory.

8. The method of claim 1, the signaling further comprising:
providing a non-visual signal to the user.

9. The method of claim 1, comprising:
providing a signal to move the probe to a new point.

10. The method of claim 1, the measuring image data comprising:
measuring image data for a range of depths with an Optical Coherence Tomography imaging system.

11. The method of claim 1, the signal comprising:
at least one of changing a color of the light beam or blinking the light beam to indicate the identified retinal tissue pathology to the user while the user views the surgical field.

12. An apparatus to determine an ophthalmic tissue pathology, comprising:
an axial scanner with a physical probe configured to be inserted into an eye and moved along a scanning line to measure retinal image data for a range of depths corresponding to a target point in an eye;
an imaging processor coupled to a memory, configured
to determine retinal image information from the image data, including identifying two or more image features in the image data that represent boundaries of tissue layers along the scanning line,
to identify a retinal tissue pathology corresponding to the target point from the image information by comparing the two or more image features representing boundaries of tissue layers at a first portion of the scanning line to the two or more image features representing boundaries of tissue layers at a different, second portion of the scanning line; and
to determine, based on the identified retinal tissue pathology, a type of the retinal tissue pathology based on retinal pathology data stored in the memory;
to generate a signal, a to indicate to a user the type of the retinal tissue pathology, wherein the signal comprises a change to a characteristic of a light beam visible in a surgical field that corresponds to the type of the retinal tissue pathology.

13. The apparatus of claim 12, wherein:
the image data is one of a reflection strength, a scattering amplitude, an absorptivity, a noise, a fluctuation, and an optical data.

14. The apparatus of claim 12, the axial scanner comprising:
an Optical Coherence Tomography imaging system.

15. The apparatus of claim 12,
wherein at least one image feature in the image data is one of a peak, valley, maximum, minimum, halfway point, transition point, and plateau of the image data as a function of depth; and wherein the imaging processor is configured to measure a depth difference between two of the identified image features, wherein the depth difference is part of the image information.

16. The apparatus of claim 12, wherein:
the imaging processor is configured to determine at least one of an existence of the tissue pathology and a thickness of the tissue pathology based on the image information.

17. The apparatus of claim 12, wherein:
the imaging processor is configured to communicate with the memory
to assemble a set of image information corresponding to a sequence of target points distributed along the scanning line; and
to determine the type of the tissue pathology by comparing the image information associated with different target points along the scanning line.

18. The apparatus of claim 17, wherein:
the imaging processor is configured to determine the type of the retinal tissue pathology by at least one of
averaging image information along the sequence of target points,
filtering image information along the sequence of target points with a Kalman filter,
using a linear regression technique,
using a principal components analysis technique and
using a lookup table correlating at least one image information to at least one tissue structure.

19. The apparatus of claim 12, wherein:
the signal further comprises a non-visual signal to the user, the non-visual signal indicating a type of the identified tissue pathology.

20. The apparatus of claim 12, wherein:
the signal comprises at least one of changing a color of the light beam or blinking the light beam to indicate the identified retinal tissue pathology to the user while the user views the surgical field.

21. An apparatus to determine an ophthalmic tissue pathology, comprising:
an axial scanner with a physical probe configured to be inserted into an eye and moved along a scanning line to measure retinal image data for a range of depths corresponding to a sequence of target points in an eye, the sequence of target points being distributed along the scanning line;
an imaging processor coupled to a memory, configured
to determine retinal image information from the image data, including identifying two or more image features in the image data that represent boundaries of retinal tissue layers along the scanning line, and
to identify a retinal tissue pathology corresponding to the target points from the image information by comparing the two or more image features representing boundaries of tissue layers at a first portion of the scanning line to the two or more image features representing boundaries of tissue layers at a different, second portion of the scanning line; and
to determine, based on the identified retinal tissue pathology, a type of the retinal tissue pathology based on retinal pathology data stored in the memory; and
a visual user indicator system inserted into the eye and configured to, generate a signal to indicate to a user the type of the tissue pathology, wherein the signal comprises a change to a characteristic of a light beam visible in a surgical field that corresponds to a the type of the retinal tissue pathology.

* * * * *